United States Patent [19]

Goetz et al.

[11] 4,345,840

[45] Aug. 24, 1982

[54] METHOD AND APPARATUS FOR INSTANTANEOUS BAND RATIOING IN A REFLECTANCE RADIOMETER

[75] Inventors: Alexander F. H. Goetz, Altadena; Richard A. Machida, La Verne, both of Calif.

[73] Assignee: California Institute of Technology, Pasadena, Calif.

[21] Appl. No.: 138,306

[22] Filed: Apr. 8, 1980

[51] Int. Cl.³ .......................... G01J 3/50; G01N 21/25
[52] U.S. Cl. .................................... 356/407; 250/339; 250/340; 350/315; 356/51; 356/418
[58] Field of Search ................ 250/339, 340; 356/51, 356/407, 416, 418, 419, 448, 320

[56] References Cited

U.S. PATENT DOCUMENTS

| | | | |
|---|---|---|---|
| 3,405,268 | 10/1968 | Brunton | 250/339 |
| 3,497,304 | 2/1970 | Berube | 356/407 |
| 3,519,816 | 7/1970 | Bartz et al. | 356/51 X |
| 3,783,284 | 1/1974 | McCormack | 250/339 |
| 3,960,452 | 6/1976 | Huebner | 356/407 |
| 4,043,668 | 8/1977 | Goetz et al. | 356/73 |
| 4,134,683 | 1/1979 | Goetz et al. | 356/407 |
| 4,266,878 | 5/1981 | Auer | 356/419 |

FOREIGN PATENT DOCUMENTS

| | | |
|---|---|---|
| 522028 | 6/1940 | United Kingdom . |
| 686594 | 1/1953 | United Kingdom . |
| 1423290 | 2/1976 | United Kingdom . |
| 1478058 | 6/1977 | United Kingdom . |
| 1548686 | 7/1979 | United Kingdom . |

*Primary Examiner*—F. L. Evans
*Attorney, Agent, or Firm*—Freilich, Hornbaker, Wasserman, Rosen & Fernandez

[57] ABSTRACT

A hand-held instrument is provided to compare information from selected infrared and visible bands in the 0.4 to 2.5 micrometer range, to perform ratioing via a dividing circuit (17) and to directly read out, via a display system (18), ratio values in a continuous digital display. The dual-beam, ratioing radiometer contains two optical trains (10, 12), each having two repeater lenses (L1a, L1b and L2a, L2b) and a cooled lead sulfide detector (D1, D2). One of the trains (10) is pivotal to facilitate measurements at distances ranging from about 1 meter to infinity. The optical trains are intersected by a set of two coaxially-mounted filter wheels (F1, F2), each containing up to five interference filters and slits to pass radiation filtered by the other. Filters with band passes as narrow as 0.01 micrometer are used in the region 0.4 to 2.5 micrometers. The total time for a calibration and measurement is only a few seconds. It is known from previous field studies using prior art devices, that materials, e.g., clay minerals, and carbonate minerals such as limestone, have unique spectral properties in the 2.0 to 2.5 micrometer region. Using properly chosen spectral filters, and ratioing the signals to remove the effect of topography on the brightness measured, the instrument can be used for real-time analysis of reflecting materials in the field. Other materials in the broader range of 0.4 to 2.5 micrometers (and even beyond) could be similarly identified once the reflectance spectrum of the material is established by any means.

9 Claims, 6 Drawing Figures

METHOD AND APPARATUS FOR INSTANTANEOUS BAND RATIOING IN A REFLECTANCE RADIOMETER

ORIGIN OF INVENTION

The invention described herein was made in the performance of work under a NASA contract and is subject to the provisions of Section 305 of the National Aeronautics and Space Act of 1958, Public Law 85-568 (72 Stat. 435; 42 USC 2457).

BACKGROUND OF THE INVENTION

This invention relates to a radiometer, and more particularly to a method and apparatus for dual band reflectance radiometry, and still more particularly to a method and apparatus for ratioing narrow bands selected to provide positive identification of reflecting materials by at least one ratio of the two prominent spectral peaks characterizing the material.

Reflectance radiometers have been successfully used in detecting various minerals—from alunite to zeolite. For example, a portable reflectance spectrometer is disclosed by Dr. Alexander F. H. Goetz, one of the present inventors, and others, in U.S. Pat. No. 4,043,668. Briefly the spectrometer disclosed there included an optical unit and a digital recording unit for recording the intensity of reflected radiation over a spectral range (0.4 to 2.5 micrometers) selected by a filter wheel. The recorded spectral data are later analyzed to determine the composition of the materials which produce the reflectance radiation spectral data. This development of a portable reflectance spectrometer followed the development in 1967-1970 of a Multispectral Photography Experiment S-158 included in the APOLLO 12 mission. That experiment utilized multispectral imaging systems with analysis capability for determination of lunar lithographic boundaries remotely from orbit, but without real-time spectral data analysis. For a description of the experiment see Alexander F. H. Goetz, et al., "Apollo 12 Multispectral Photography Experiment," *Geochimica Acta*, Vol. 3, 2301-2310, MIT Press, 1971.

Following that development, new research programs were established in 1970-1973 to improve the accuracy of telescopic spectroradiometric imaging systems. The role of computer image processing in orbital multispectral photography was established as a means of enhancement. The first preliminary geologic investigations were undertaken in the field on the Colorado plateau to evaluate and interpret earth satellite (ERTS-1) multispectral data, suitably enhanced. Studies were also carried out to determine the quality and use of ERTS radiometric information with reference to arid desert regions. See Alexander F. H. Goetz, et al., "Symposium," Mar. 5-9, 1973 NASA SP-327 at pages 403 to 411, and 1159 to 1167. Also Proceedings of the 4th Annual Conference on Remote Sensing in Arid Lands, 136-147, Univ. of Arizona, Tucson, Nov. 1973. The image enhancement technology used in this effort is discussed in a NASA New Technology Report, NPO-10541.

An earth applications effort was formally organized at the Jet Propulsion Laboratory (JPL) of the California Institute of Technology. A novel portable reflectance spectrometer was developed for the 0.4 to 2.5 micrometer range, also with digital recording in the field. This instrument is the subject of the aforesaid U.S. Pat. No. 4,043,668, assigned to California Institute of Technology. The electronic recording unit was a separate "backpack" system, with an inherent time delay prior to actual mineral identification. The unit did not incorporate features of the present invention, and had no real time readout capability for analysis, but was capable of recording about 200 spectra per day on compact digital tape cassettes using two persons in the field.

Increased activity from 1975-1978 in the field of multispectral imaging and analysis systems at JPL led to the development of systems with CCD imaging devices, readily interfaced with more rapid computer analysis and readout systems, as is more fully discussed in U.S. Pat. No. 4,134,683, by Alexander F. H. Goetz, et al. An imaging system including several arrays of charge coupled devices (CCD), or linear detector arrays, were used to obtain simultaneously spectral reflectance data at different wavelengths for a target area using a plurality of filters, each accommodating a particular bandwidth. Data from the arrays are recorded and later read out in parallel to a computer or microprocessor.

The microprocesor made it possible to analyze image data in real time, and to display the information superimposed on an image of one to provide geographic locations. However, generally speaking, fairly broad visible and near-IR bands were covered and only rough qualitative analysis of minerals or oil spill zones was possible. The system was not portable and could be programmed to look for only one specific material at a time.

The instrument of U.S. Pat. No. 4,134,683 included "band ratioing" using divider circuits. "Band ratioing" is a technique which seeks to provide positive identification of materials by measurement or calculation of ratios of the two most prominent spectral peaks, rather than a single peak, characterizing the material. Band ratioing thus creates ratios of two filtered channels to cancel out topographic effects, etc. Band ratioing is also helpful in dealing with the problem of high data correlation between channels caused by systematic effects such as topography.

The prior art discussed above provided a portable reflectance radiometer without real-time data processing, or a nonportable multichannel reflectance imaging radiometer with limited real-time data processing. There has been no reflectance radiometer with instantaneous, real-time data processing, nor has there been a portable instrument with the capability of monitoring different peaks continuously without obtaining a full spectrum. And finally there has been no portable instrument provided to monitor a selected few narrow band peaks simultaneously and, through instantaneous band ratioing of one band channel versus the second band channel for at least one ratio, identifying the nature of the material reflecting the radiation. Yet the experience with the above-cited prior art devices, when applied to mineral identification problems in the field, makes it clear that for rock or mineral classes, such as carbonates and silicates, instantaneous identification would be possible if a portable unit could provide instant band ratioing. A new kind of instrument has therefore been needed to give useful information directly at the sensor and in real time for instantaneous rock identification. It is the intention of the present invention to provide such a new kind of instrument.

SUMMARY OF THE INVENTION

Briefly described, the present invention involves a ratioing radiometer able to identify selected materials that reflect radiation within a predetermined band. The instrument is particularly suited for differentiating between the clay minerals most commonly found in the earth's terrain. The instrument is a self-contained, dual-beam ratioing radiometer with two optical trains directed at the same target. It provides a continuous digital readout of ratio values from the two optical trains each of which includes a separate filter for selection of the narrow spectral bands to be ratioed for identification of the presence of a particular mineral on the basis of known spectral characteristics of the mineral. In an exemplary embodiment, the narrow bands ratioed are selected infrared and visible bands in the 0.4 to 2.5 micrometer range, and means are provided for pivoting the axis of at least one optical train with respect to the other, in order that both have their axis directed at the target. Each optical train channel has two relay (repeater) lenses with a selectable filter between the lenses, and a detector at the rear. As a particular feature of the invention, two coaxial filter wheels serve the separate channels by providing slits in one filter wheel between filters to pass light to the selected filter in the other wheel, and slits in the other filter wheel between filters to pass light already directed through a selected filter on to a relay lens and detector. In that way, one filter wheel can be rotated independently of the other to position a selected filter in the light path between relay lenses while a slit in the other filter wheel passes the filtered light through to the second relay filter and detector. Alternatively, both filter wheels may be turned together, as when the paired filters for particular minerals have been selected and properly disposed on the filter wheels. Operation to check for the presence of the different minerals in the target area can then be simplified by stepping both filter wheels together through all positions, for example five, such that for each position each filter wheel presents a different filter paired with a filter in the other wheel. Pivoting an optical train can then be readily accomplished by, for example, a cam at the front end operating on the bracket of the pivotal optical train to pivot its axis on a pivot point between the slit and filter through which the optical axis of the pivotal optical train passes. The pivotal optical train bracket carries the two relay lenses and, behind the second relay lens, a detector. A chopper in front of both channels serves to chop the radiation to the detectors in order that known AC amplification and synchronous detection techniques be used. Continuous ratioing of the two detector outputs (division of the detector output of one channel by the detector output of the other channel), and continuous digital readout of the ratio for display or recording, permits continuous and instantaneous identification of the material in the reflecting surface.

The novel features that are considered characteristic of this invention are set forth with particularity in the appended claims. The invention will best be understood from the following description when read in connection with the accompanying drawings.

DESCRIPTION OF PREFERRED EMBODIMENTS

Figure 1:
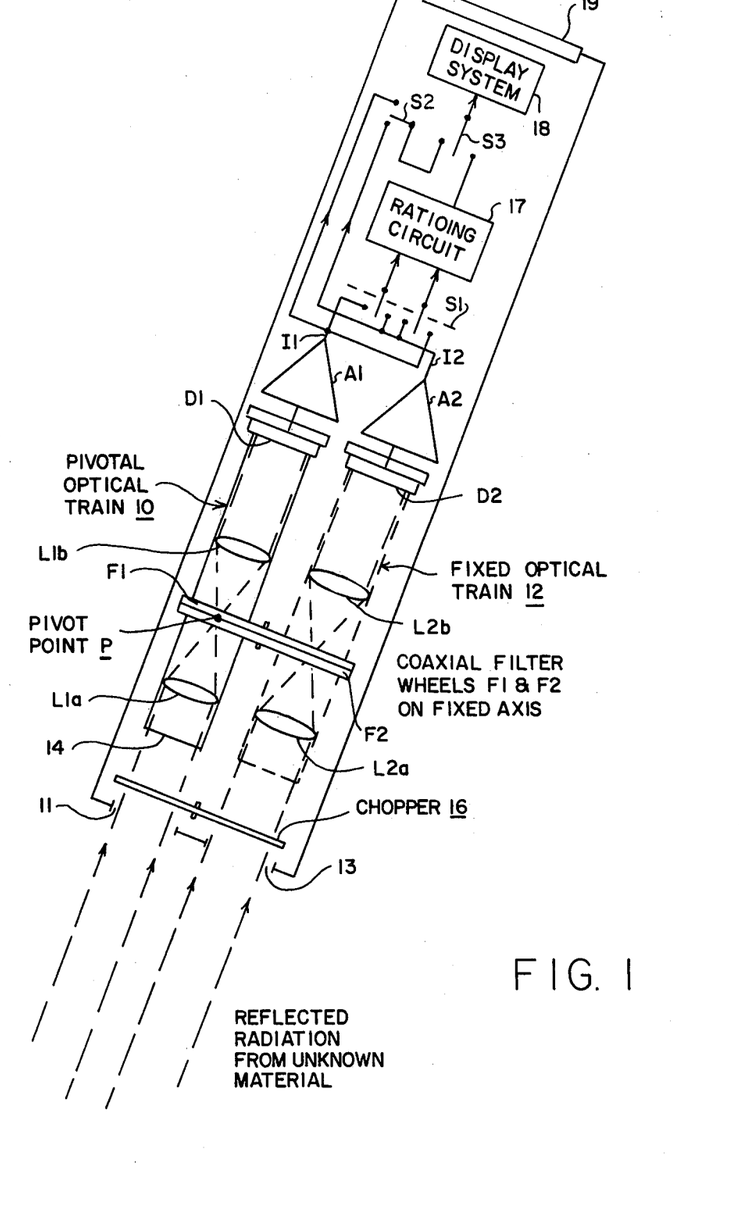
FIG. 1 is a simplified schematic diagram of a dual-beam ratioing radiometer for use at distances from one meter to virtual infinity in accordance with the present invention.

Referring now to FIG. 1 of the drawings, a simplified schematic diagram of a dual-beam ratioing radiometer embodying the principles of this invention is disclosed. The radiometer includes two channels, a first channel comprised of an optical train 10, slit 11, cooled, lead-sulfide detector D1 and amplifier A1, and a second channel consisting of an optical train 12, slit 13, cooled lead-sulfide detector D2 and amplifier A2. The optical train 10 is mounted on a bracket represented by a solid line 14 in order to pivot its optical axis about a point P. Mounted on the bracket are relay (repeater) lenses L1a and L1b, as well as the detector D1. The slit 11 is wide enough to allow radiation entering an instrument enclosure (represented by a solid line 15) to be picked up by the lens L1a over the full pivotal angle, which is small enough to aim its axis at the same point on the target as the axis of the fixed optical train 12 for operation at close range (about 1 meter). For a greater range, the pivotal optical train may be adjusted for an even smaller angle with the axis of the fixed optical train, and for a great (virtually infinite) range, that angle is reduced to zero to place both optical train axes parallel to each other.

In practice, the pivotal optical train will be provided with a knob operated cam to place its axis at either of the extreme positions, namely at "one meter" and at "infinity," since the instrument will be used either by an operator on foot who will aim it directly at the ground, or an operator in a vehicle who will aim it at the ground from a great distance, such as 100 meters or more. The space of a few centimeters between the two optical trains is so small, as compared to the great distance of about 100 meters, that for all practical purposes, the axes of the two optical trains will be aimed at the same point, i.e., both optical trains will receive reflected solar radiation from the same target area when their axes are parallel. This "two stop" adjustment is thus easily made without any need to measure or estimate range to the target.

Included in the instrument housing is a chopper 16 to convert the DC signals entering the instrument to AC signals at the detectors D1 and D2 using AC amplifiers A1 and A2. Synchronous detection of the amplitude of the two AC signals I1 and I2 may be employed if desired. In any case, the amplitudes of the signals A1 and A2 are detected and ratioed in a dividing circuit 17. An analog dividing circuit is assumed in this simplified diagram, but the detected signals I1 and I2 could be periodically converted to digital form in order to use digital techniques to form the ratio. If an analog dividing circuit is employed, then the ratio I1/I2 is periodically converted to digital form for display using a conventional display system 18. The operator then reads the value of the ratio from the display through a window 19, and from that value immediately determines the reflecting material in the target area. Reference is repeatedly made throughout this description to reflecting material, generally because this dual-band ratioing radiometer could be used to detect, for example, radiation from grain in a bin, or from vegetation, to determine moisture content, and not just to determine the mineral content of the earth's reflecting target area.

This ratioing technique provides positive identification of reflecting material by calculation of the ratio of at least two of the most prominent spectral peaks of the reflectance spectrum for the particular material. The ratio may be of the spectral peaks only, using very narrow band filters, or the ratio may be of the band wings, i.e., the slopes of the peaks. Either characteristic may be ratioed. In either case a second ratio using another set of spectral characteristics may be required in order to resolve any ambiguity with respect to another material having one characteristic ratio that is very near a characteristic ratio of the material of interest. It should be noted that the band-wing characteristic is a ratio of the intensity of one band wing to the intensity of another band wing, and not a ratio of actual peak slopes, where the slope is defined as $\Delta I/\Delta \lambda$, but rather of average peak slopes over the filter bands. To select the spectral characteristic (peak or band wing) to be ratioed, dual coaxial filter wheels F1 and F2 are so adjusted (on a fixed axis between the two channels that is parallel to the optical axis of the fixed train 12) as to provide band filtering of the reflected radiation centered on the two peaks chosen for ratioing based upon prior knowledge of the characteristic spectrum of the material, as will be described more fully hereinafter. Each filter wheel may have as many as five filters, which provides a maximum of 25 possible distinct ratios, although in practice only a more limited number may be useful, such as the band ratios shown in the following table.

| BAND-RATIO | ALUNITE | KAOLINITE |
|---|---|---|
| 2.10/2.17 | 1.47 | 1.59 |
| 2.10/2.22 | 0.86 | 1.41 |
| 2.17/2.20 | 0.80 | 1.10 |
| 2.17/2.22 | 0.59 | 0.88 |
| 2/20/2.22 | 0.74 | 0.80 |
| 2.20/2.35 | 0.74 | 0.95 |

| BAND-RATIO | MONTMORILLONITE | CALCITE |
|---|---|---|
| 2.10/2.17 | 1.04 | 1.02 |
| 2.10/2.22 | 1.19 | 1.04 |
| 2.17/2.20 | 1.20 | 1.00 |
| 2.17/2.22 | 1.14 | 1.02 |
| 2.20/2.22 | 0.94 | 1.03 |
| 2.20/2.35 | 1.01 | 1.27 |

Thus, by providing two optical trains or channels for signal ratioing and instantaneous digital readout of channel intensity ratios, immediate and real time identification of minerals is made possible. All that is required to identify a particular material is to select the proper filters in the two filter wheels. The filter wheels turn on a common axis; therefore spaced slits are provided in each to pass the light of the wavelength selected by the filter in the other, as will be described more fully hereinafter with reference to FIGS. 2 and 3. In that manner, predetermined bandwidth filtering combinations known to provide optimum analysis results in ratioing of the respective channel intensities, one against the other.

It would be desirable to sometimes expand the scale of a particular ratio, or to conduct a linearity check of the instrument. This can be done by inverting the ratio of I1/I2 to I2/I1. To accomplish that, a double-pole double-throw switch S1 may be placed in its second position where the same detector outputs yield the same ratio inverted. In either position, there is an instantaneous display of the ratio of intensity in the two channels. In addition, a switch S2 may be provided, with a switch S3, to select either one of two channels for display instead of the ratio output. This is useful in calibrating the instrument.

Calibration is carried out with solar radiation or an artificial source, such as a quartz-iodine lamp and a highly reflective reference material having a uniform spectral reflectance in the region of interest. A suitable reference material is white ceramic wool sold commercially as Fiberfax, as described in the aforesaid U.S. Pat. No. 4,043,668. The gain of the amplifier in one channel is first adjusted to some intermediate value between zero and maximum. The intensity value display for that channel can be read to determine when that has been achieved. Then the switch S3 is placed in proper position for display of the ratio, and the gain of the second amplifier is adjusted so that the display shows "1.00". While this is being done, any pair of filters may be used. Typically only one calibration per hour is necessary during the middle of the day when solar radiation conditions are not subject to rapid change. However, a quick check for a standard ratio reading of the Fiberfax reflection may be made after band ratio reading of the unknown surface to confirm accuracy of the ratio.

An exemplary embodiment of the concepts described with reference to FIG. 1 will now be described with reference to FIGS. 2 through 5. For convenience in correlating the structure of the exemplary embodiment with elements in the simplified schematic diagram of FIG. 1, all numerals used to refer to elements in FIG. 1 will be applied as reference numerals to the corresponding elements in the structure of FIGS. 2 through 5, with additional reference numerals applied to elements not appearing in FIG. 1.

Figure 2:
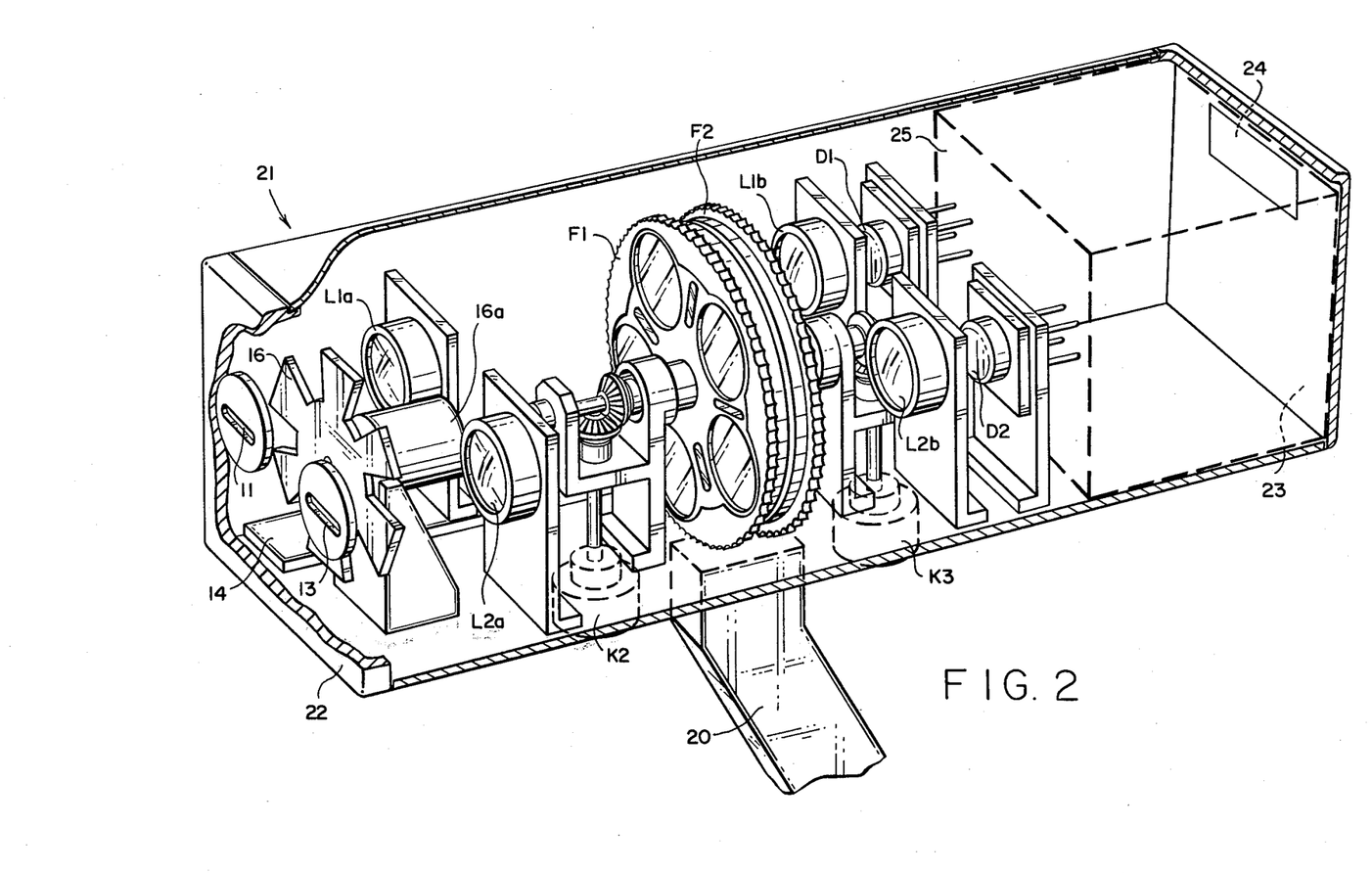
FIG. 2 is an isometric schematic diagram of the optical system of FIG. 1.

In FIG. 2 there is shown an isometric schematic diagram of a hand-held dual-band ratioing reflectance radiometer comprised of a handle 20 attached to the floor of an enclosure 21 having two sides and a top besides a floor, and having two end plates, a front end plate 22 having slits 11 and 13, and a rear end plate 23 having a window 24 for numeric display of the ratio values. An electronic package (represented by a dashed line box 25 at the rear of the instrument includes printed circuit boards for the amplifiers A1 and A2, dividing circuit 17, and display system 18. The necessary switches S1 through S3 may be conveniently mounted on the rear plate 23 below the display window 24. The gain control knobs for the amplifiers, coaxial connectors for recording either channel and the ratio of the two channels, if desired, and a connector for a power cable from a battery pack may also be conveniently mounted on the rear plate 23 below the display window 24. Between the front end plate 22 and the electronic package, there are suitable brackets secured to the floor of the enclosure 21 for mounting other elements. These other elements are the chopper 16 and drive motor 16a. Note that the motor is placed with its axis on the center line between the two optical trains which begin with the lenses L1a and L2a, and conclude with detectors D1 and D2 behind lenses L1b and L2b.

The elements of the pivotal optical train comprised of lens L1a, lens L1b and detector D1 are mounted on a bracket 14 which pivots on a point between filter wheels F1 and F2. The bracket is arranged to be clear of the filter wheels so that they may be stationary while the pivotal optical train pivots on a plane between the two filter wheels. This is desirable because the coaxial filter wheels do not pivot with the pivotal optical train, but instead remain fixed in a position normal to the axis of the fixed optical train.

Figure 3:
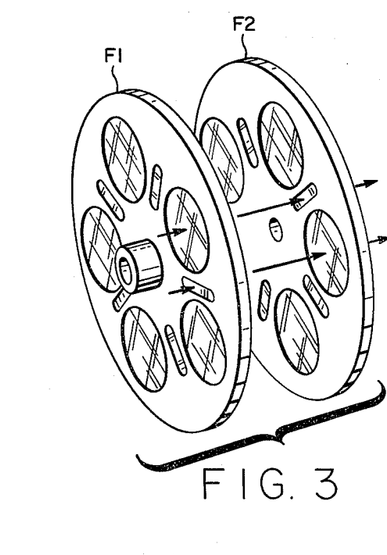
FIG. 3 illustrates the arrangement of two coaxial filter wheels having spaced slits and filters which intercept the dual beams of the ratioing radiometer shown in FIGS. 1 and 2.
Figure 4:
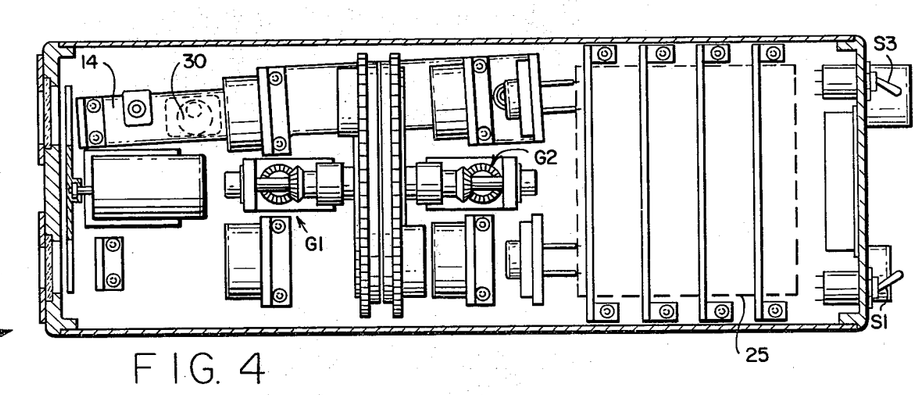
FIG. 4 illustrates in a plan view the ratioing radiometer of FIG. 2.
Figure 5:
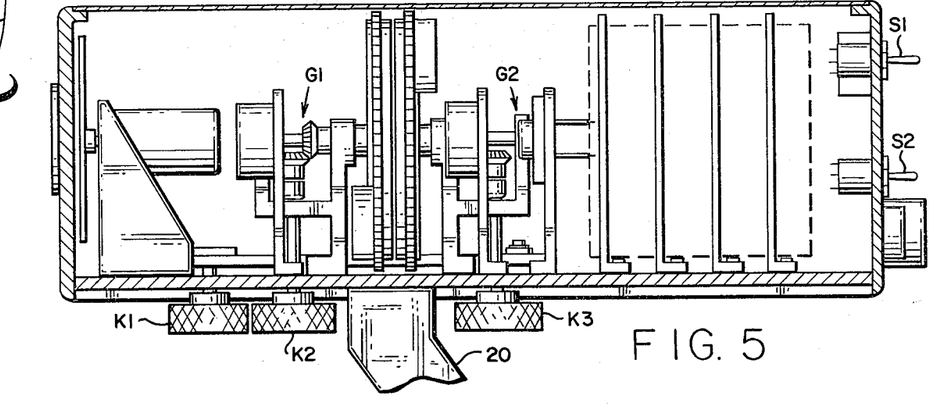
FIG. 5 illustrates in a vertical sectional view the ratioing radiometer of FIG. 4.

The two filter wheels are shown separated in FIG. 3 to make clear that one wheel (F2) which serves the fixed optical train 12 has a filter disc in optical alignment with a slit in the other filter wheel (F1) which serves the pivotal optical train 10. Diametrically opposite the optical axis of the fixed train 12, a filter disc in the wheel F1 is positioned in the optical axis of the pivotal train with a slit directly behind it in the filter wheel F2. The slit and filter disc are sufficiently wide to accommodate the beam being directed by the relay lens L1a to the relay lens L1b for all pivotal positions. The range of pivotal positions is quite limited, as may be appreciated from the plan view of FIG. 4, but such limited pivotal motion is sufficient to converge the optical axis of both trains on the same target area from a range of 1 meter to infinity. As noted hereinbefore, only the two extremes in range are of real interest. Consequently, a cam 30 (FIG. 4) is provided to pivot the bracket 14 to one extreme in one position and to the other extreme in the other position by simply turning the cam 180° by a knob K1 (FIG. 4). Two additional knobs K2 and K3 are provided to turn gear trains G1 and G2 that turn the filter wheels F1 and F2, respectively. Detents are provided for the filter wheels to set them in proper registration for each of five selectable positions for each of five filter discs. Gear teeth on the rims of the filter wheels are provided to engage a gear (not shown) which causes both wheels to be turned together by turning either knob K2 or K3. A fourth knob, K4, selectively positions this additional gear (not shown) into engagement for this feature. Such a feature would be useful when all five filter discs of one wheel for one channel have been paired with filter discs of the other wheel for the other channel. In that case it is simpler to step both wheels together through all five positions.

In summary, operation of the instrument will be reviewed. The instrument is first calibrated as described hereinbefore using solar radiation or an artificial source reflected from a reference material. For this calibration, a piece of reference material is held at a range of about one meter. Then the instrument is ready for field use. Actually, the calibration is done in the field just prior to use. This will usually be during the middle of the day, rather than early morning or later afternoon, so that recalibration is not necessary after each use, but instead only after each lapse of about one hour, although the calibration procedure may be carried out to confirm that a particular ratio is correct, i.e., is made with the instrument properly calibrated.

Figure 6:
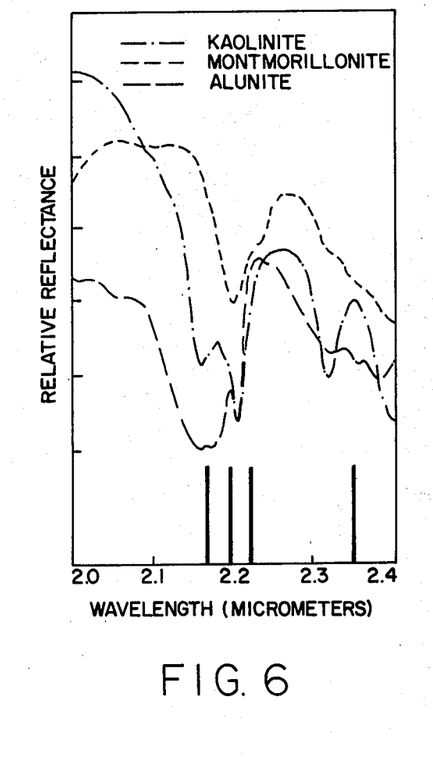
FIG. 6 illustrates radiation reflectance spectra of selected minerals with bars indicating the location of centers of four narrow filtered bands which may be ratioed in different paired combinations to determine minerals of the reflecting target area in the system of FIGS. 1 to 5.

On the basis of known spectral signatures, this exemplary instrument can be used to compare information from selected infrared and visible bands in the 0.4 to 2.5 micrometer range, to perform ratioing, and to directly read out ratio values in a continuous digital display. What makes this possible is the dual-beam, ratioing radiometer organization of FIG. 1 which contains two optical trains, each having two repeater lenses and a cooled lead-sulfide detector. The optical trains are intersected by a set of two, coaxially-mounted, filter wheels each containing a plurality of interference filters. Filters with band passes as narrow as 0.01 micrometer are used in the range of 0.4 to 2.5 micrometers. The total time for a calibration and measurement is only a few seconds. It is known from previous field studies using devices, such as the reflectance spectrometer of U.S. Pat. No. 4,043,668 referenced above, that clay minerals and carbonate minerals such as limestone have unique spectral properties in the 2.0 to 2.5 micormeter region. FIG. 6 shows the observed relative reflectance for kaolinite, montmorillonite, and alunite in this region. The present invention, using properly chosen spectral filters, and ratioing the signals to remove the effect of topography on the brightness measured, can be used as an analytical tool in the field over this region as well as over the broader range. In FIG. 6, a series of bars have been added to indicate suitable locations of the spectral centers of the dual-beam channel filters, adapted for clay mineral analysis.

By using properly chosen spectral filters in this more limited region of 2.0 to 2.5 micrometers, and by ratioing the signals to remove the effect of topography on the brightness measured, a number of materials can be identified uniquely. The table set forth above illustrates more specifically the prior art data tabulation required. For example, montmorillonite and kaolinite yield very different ratio values for filters centered at 2.10 and 2.17 micrometers. Therefore, by directly displaying the ratio of brightness for two filters at these wavelengths, it becomes possible to have the ratio value provide an index number for analytical identification in field geology studies.

The above example in this more limited region illustrates the method of operation of the present invention with real time display of the ratio of reflected radiation intensity values as between the two optical trains. It will be understood that the same instrument can be used to indicate the reflected radiation intensity value in a single optical train, as noted above. The ability to obtain instant results in the field, rather than taking samples to the laboratory, provides a powerful field prospecting capability, either by an operator on foot, or in a land or air vehicle.

From the foregoing description, it is evident that the present invention provides instantaneous, real-time data processing for the reflected radiation intensity of one or more pairs of channels in narrow bands without obtaining the full spectrum data. More particularly, the present invention monitors at least two selected and different narrow bands continually, and provides an instantaneous ratioing of the intensities of the two channels with instantaneous digital read out. More than one pair may be simultaneously monitored in other dual channels. This ratioing represents a new class of instrument. Examples in the region of 2.0 to 2.5 micrometers is given by way of explanation, and not limitation. The broader range of 0.4 to 2.5 micrometers, and beyond, could be used to identify any material once the refletance spectrum is established by any means known or to be devised. Also the use of solar radiation to illuminate the target is a matter of convenience in the field. In some special applications, any radiation source may be used provided only that it include the narrow bands of interest. Still other modifications, equivalents and variations will occur to those skilled in the art. Consequently, the following claims are intended to include such modifications, equivalents and variations.

What is claimed is:

1. A method for providing instantaneous identification of particular reflecting materials by ratioing reflectance measurements at selected pairs of wavelength bands, each band of a pair being chosen for a particular spectral characteristic of a material of interest selected from a group consisting of spectral peaks and band wings on either side of spectral peaks for each band reflected from a particular material, comprising the steps of selecting a plurality of different paired bands, one pair at a time, for instantaneous band ratioing, simultaneously detecting the intensity of radiation reflected by materials under investigation into said plurality of predetermined bands centered on spectral characteristics of the different materials, determining the ratio of radiation intensity in at least one band to the radiation intensity in other bands, and displaying the band ratio thus determined to provide a ratio display indicative of the particular material, whereby a reflecting body can be checked for the presence of a plurality of different materials identified by at least one particular band ratio value for each material.

2. A method as defined in claim 1, wherein said spectral characteristics of said materials are spectral peaks.

3. A method as defined in claim 1 wherein said spectral characteristics of said material are band wings consisting of a measurement of intensity measurements on either side of spectral peaks characterizing said material.

4. Apparatus for identifying an unknown material in a target area that reflects radiation within predetermined selected bands comprising two optical trains directed independently at the same target area, each train having a detector for measuring the intensity of radiation reflected from the same target area, and each train having a suitable filter for passing a different one of a set of selected bands of reflecting radiation, each one being selected to be centered on different spectral characteristics of the material, means for producing the ratio of reflected radiation intensity detected through the detector of one optical train to the reflected radiation intensity detected through the detector of the other optical train for each set of selected bands, and means for displaying the value of said ratios, whereby said particular material is identified by a particular ratio value.

5. Apparatus as defined in claim 4 including means for adjusting said two optical trains to receive radiation from the same target area for different distances from the target area.

6. Apparatus as defined in claims 4 or 5 including means for selectively positioning one of a plurality of filters on the optical axis of each of said optical trains for each of a plurality of materials to be identified, each material by a unique band ratio displayed.

7. Apparatus as defined in claim 4 or 5 including two coaxial filter wheels positioned with their axes between and parallel to the optical axes of said optical trains, said filter wheels having spaced slits and filters arranged so that a slit in one wheel and a filter in the other wheel will be aligned with the axis of one optical train, and a filter in said one wheel and a slit in the other wheel will be aligned with the axis of the other optical train, whereby one of a plurality of filters is selected in each of said optical trains for each of a plurality of materials to be identified, each material by a unique band ratio displayed.

8. Apparatus as defined in claim 4 or 5 wherein said spectral characteristics of said material are spectral peaks.

9. Apparatus as defined in claim 1 or 5 wherein said spectral characteristics of said material are band wings consisting of a measurement of intensity measurements on either side of spectral peaks characterizing said material.

* * * * *

UNITED STATES PATENT AND TRADEMARK OFFICE
CERTIFICATE OF CORRECTION

PATENT NO. : 4,345,840
DATED : August 24, 1982
INVENTOR(S) : Alexander F.H. Goetz and Richard A. Machida It is certified that error appears in the above-identified patent and that said Letters Patent are hereby corrected as shown below:

Column 4, line 63, after "D2" insert -- for amplification --

Column 5, line 51, "2/20/2.22" should be -- 2.20/2.22 --

Column 6, line 6, after "results" insert -- are used --

Column 8, line 21, "micormeter" should be -- micrometer --

Column 10, line 40, after claim delete "1" and substitute -- 4 --

Signed and Sealed this

Ninth Day of November 1982

[SEAL]

Attest:

Attesting Officer

GERALD J. MOSSINGHOFF
Commissioner of Patents and Trademarks